United States Patent [19]
Callaghan

[11] Patent Number: 5,271,393
[45] Date of Patent: Dec. 21, 1993

[54] PACEMAKER EMPLOYING ANTITACHYARRHYTHMIA PREVENTION BASED ON VENTRICULAR GRADIENT

[75] Inventor: Francis J. Callaghan, Miami, Fla.

[73] Assignee: Telectronics Pacing Systems, Inc., Englewood, Colo.

[21] Appl. No.: 696,041

[22] Filed: May 6, 1991

[51] Int. Cl.$^5$ ............................................. A61N 1/362
[52] U.S. Cl. .......................................... 607/14; 607/26
[58] Field of Search ................................... 128/419 PG

[56] References Cited

U.S. PATENT DOCUMENTS

| | | | |
|---|---|---|---|
| 4,759,366 | 7/1988 | Callaghan | 128/419 PG |
| 4,759,367 | 7/1988 | Callaghan | 128/419 PG |
| 4,766,900 | 8/1988 | Callaghan | 128/419 PG |
| 4,905,708 | 3/1990 | Davies | 128/705 |

FOREIGN PATENT DOCUMENTS

| | | |
|---|---|---|
| 0232528 | 12/1986 | European Pat. Off. |
| 0327427 | 1/1989 | European Pat. Off. |
| 0334675 | 3/1989 | European Pat. Off. |

OTHER PUBLICATIONS

"Characteristics and Possible Mechanism of Ventricular Arrhythmia Dependent on the Dispersion of Action Potential Durations"—Kuo.

"The Ventricular Depolarization Gradient: Effects of Exercise, Pacing Rate, Epinephrine, and Intrinsic Heart Rate Control on the Right Ventricular Evoked Response"—Callaghan.

Primary Examiner—William E. Kamm
Assistant Examiner—Scott M. Getzow
Attorney, Agent, or Firm—Gottlieb, Rackman & Reisman

[57] ABSTRACT

An anti-tachyarrythmia pacing system is disclosed which utilizes an intra-cardiac electrode to obtain a gradient for each cardiac cycle. When the gradient increases beyond a predetermined value, it is determined that tachyarrythmia is imminent and the pacing system responds by pacing the heart in a therapeutic manner to prevent the onset of such tachyarrythmia.

20 Claims, 3 Drawing Sheets

PACEMAKER EMPLOYING ANTITACHYARRHYTHMIA PREVENTION BASED ON VENTRICULAR GRADIENT

TECHNICAL FIELD

This invention relates to cardiac pacing systems, and more particularly to an improved cardiac pacing system for detecting an impending onset of tachyarrythmia and preventing it from occurring.

DESCRIPTION OF THE PRIOR ART

Implantable pacemakers have many parameters which are normally set by a physician. Such parameters include voltage output, pulse width, sensitivity, etc. Additionally, most implantable pacemakers may be programmed to operate in various modes such as VVIR, VVI, VDD, etc.

Recently, emphasis has been placed on adaptive pacing; i.e., dynamically changing the parameters in response to physiological changes in the patient. One such pacemaker is disclosed in U.S. Pat. No. 4,878,497 issued to Frank J. Callaghan on Nov. 7, 1989. In the '497 arrangement, the QRS waveform is integrated to obtain the depolarization gradient. The system then compares the depolarization gradient magnitude of one cardiac cycle with the depolarization gradient magnitude of at least one previous cardiac cycle. A change in the value of the depolarization gradient is an indication of a change in cardiac stress level and is inversely proportional thereto. Thus, an increased cardiac stress level resulting from exercise, for example, will be accompanied by a decrease in the depolarization gradient. Accordingly, when the depolarization gradient magnitude decreases, means are provided to increase the pacing rate, thereby increasing the patient's heart rate and cardiac output. Conversely, when the depolarization gradient magnitude increases, such an increase is indicative of less cardiac stress and the pacing rate decreases, thereby slowing the patient's heart rate. Thus, if the patient climbs a flight of stairs, for example, the pacing rate will increase. Conversely, when he sits down and relaxes or goes to sleep, the pacing rate will decrease. While the system provides some dynamic range of the pacing rate, the system cannot recognize nor correct for pathologically fast rhythms, e.g., tachyarrhythmia. Thus, there exists a need for pacemaker technology which can recognize conditions indicating an impending onset of tachyarrhythmia and, in response thereto, pace the heart in an appropriate manner to prevent the tachyarrhythmia from even occurring.

One possible design concept for a pacing system that monitors electrocardiac activity to detect the physiological precursors of tachyarrhythmia is described in an article entitled "The QT Sensitive Cybernetic Pacemaker—A New Role For An Old Parameter" by Puddu et al. in Pace Magazine, Volume 9, January–February 1986. The Puddu article first describes a parameter commonly termed "cardiac dispersion" or simply "dispersion". The value of the dispersion is indicative of the inhomogeneity in ventricular activation-recovery properties. Dispersion normally decreases with increased heart rate. While relatively low levels of dispersion are acceptable, and indeed are present in most human hearts, a high level of dispersion due to disparate ventricular recovery times is associated with imminent tachyarrhythmia. Moreover, if dispersion is reduced to below a critical value, it is nearly impossible for tachyarrhythmia to occur, even when induced intentionally by a physician for diagnostic purposes. The Puddu article further suggests that a measure of dispersion can be obtained by measuring the QT interval, i.e., as the QT interval increases, so does dispersion.

In accordance with the above theories, the article describes a pacing system whereby the QT interval is measured during successive cardiac cycles, and when the QT interval is prolonged beyond a predetermined value, it is determined that dispersion is nearing a critical value and that tachyarrhythmia is about to occur. At this point, the pacing rate is increased significantly in order to decrease dispersion within the heart. The decreased dispersion results in much less vulnerability to, and even prevention of, tachyarrhythmia.

While the arrangement suggested by Puddu shows promise in preventing sudden death of patients due to tachyarrhythmia, the problem is that the QT interval must be measured accurately and a dispersion measure obtained therefrom. With existing technology, this is extremely difficult for several reasons. For example, the QT interval includes not only ventricular recovery time, but also ventricular activation time. As a result, the QT interval might be prolonged by any lengthening of ventricular conduction whether accompanied by changes of ventricular recovery properties or not. Other problems with measuring the QT interval are described in the Puddu article at pages 110 and 111.

In view of the above, there exists a need in the prior art for recognizing cardiac dispersion and for pacing the heart in a therapeutic manner to prevent the onset of the tachyarrhythmia indicated by such increased dispersion.

SUMMARY OF THE INVENTION

The above problem is overcome in accordance with the present invention which relates to an improved cardiac pacing system that can accurately detect physiological conditions normally present just prior to tachyarrhythmia and can pace the heart in a therapeutic manner to prevent the onset of the tachyarrhythmia. In the preferred embodiment, the QT waveform is monitored and integrated during each cardiac cycle, thereby obtaining a ventricular gradient for that cycle. When the ventricular gradient is above a predetermined value, it indicates that dispersion in the heart has reached a dangerously high value and therefore, an attack of tachyarrhythmia is about to occur. At this point, the pacing rate is increased to effect a decrease in dispersion, thereby preventing the tachyarrhythmia. By detecting increased dispersion from the ventricular gradient, tachyarrhythmia can be prevented with readily available technology, and the problem of accurately measuring the QT time interval is overcome. Also, the QT interval is non-specific in that it is influenced by activation, e.g. QRS complex, whereas ventricular gradient is not so influenced.

While the preferred embodiment utilizes the entire ventricular gradient, it should be noted that any cardiac gradient may be used. For purposes of this disclosure, cardiac gradient as used hereafter means the integral of any portion of an electrocardiac response.

DETAILED DESCRIPTION

Figure 1:
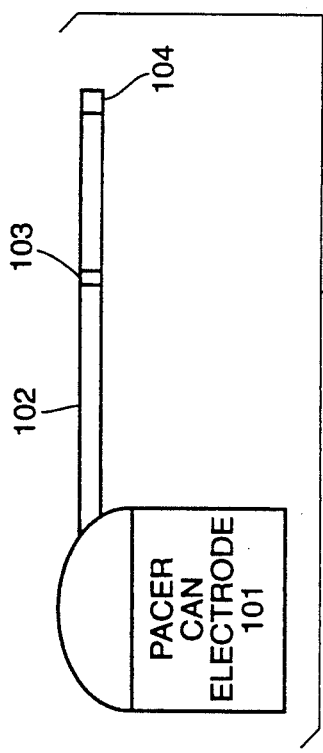
FIG. 1 is a high level block diagram of a typical pacing system.

Referring now to FIG. 1, there is shown a pacing system 100 including pacer can electrode 101, lead 102 and two electrodes, ring electrode 103 and tip electrode 104. Lead 102 is a pervenous bipolar lead that may be fabricated using conventional techniques well-known in the art. Tip electrode 104 and ring electrode 103 are each in electrical communication with a separate conductor and may be constructed using well-known techniques. The pacing system 100 can thus be viewed as a three terminal device comprising electrodes 103 and 104 and a ground terminal, normally the pacer can 101. Other details of pacing system 100 are set forth in U.S. Pat. No. 4,878,497, the teachings of which are incorporated herein by way of reference.

Figure 2:
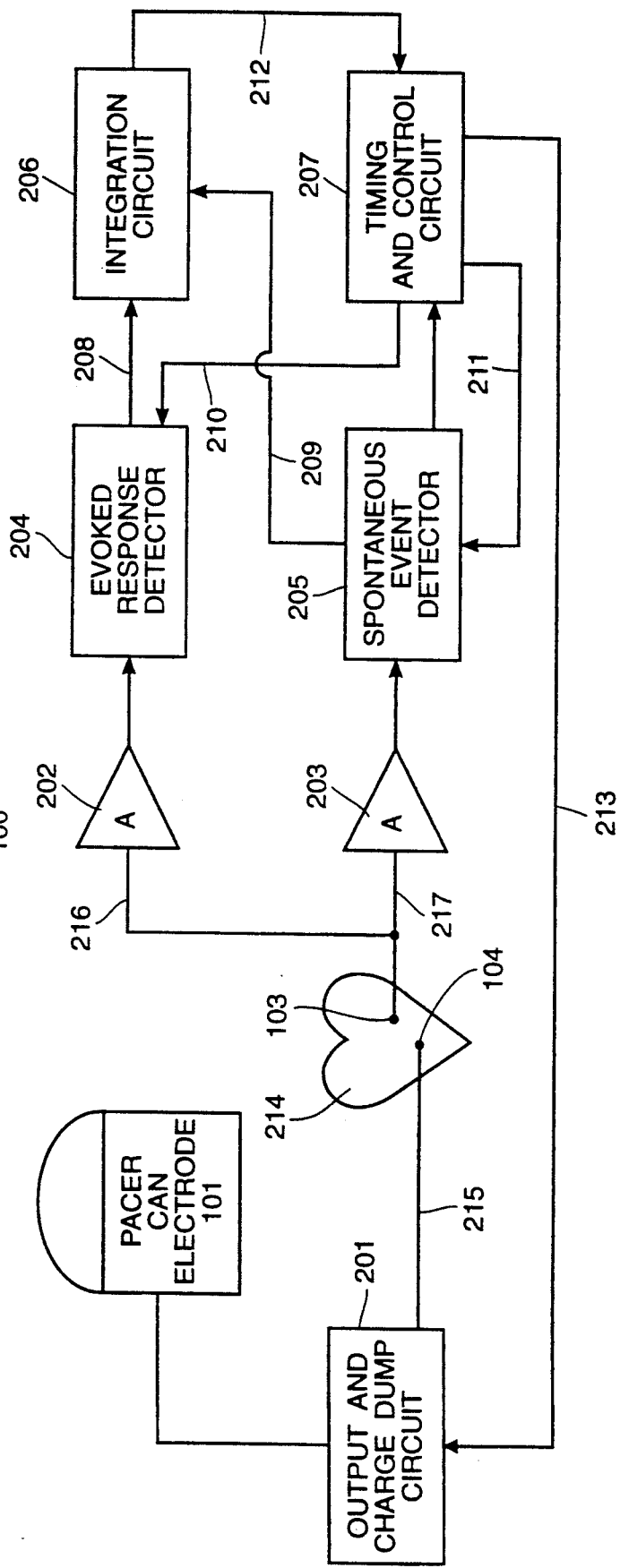
FIG. 2 shows the pacing system of FIG. 1 in greater detail and coupled to a patient's heart.

Referring now to FIG. 2, the pacing system of FIG. 1 is shown coupled to a patient's heart, the heart being shown schematically as 214. The system of FIG. 2 is responsive to electrical activity detected in the heart whether such electrical activity results from natural cardiac activity, or from cardiac activity evoked by pacing system 100.

In operation, a pulse request is transmitted from timing and control circuit 207 via conductor 213 and in response thereto, a pacing pulse is emitted from pacing system 100. The pacing pulse travels from output and charge dump circuit 201 via conductor 215 and discharges into the patient's heart 214 via tip electrode 104. The resulting electrocardiac activity is received by ring electrode 103 and is transmitted to amplifiers 202 and 203 via conductors 216 and 217, respectively. The evoked electrocardiac activity is also received by timing and control circuit 207 via conductor 210 or a separate conductor (not shown).

Evoked response detector 204 is then activated by timing and control circuit 207 and a window of time, denoted herein a response window, is opened, during which the electrocardiac response of the heart will be monitored by evoked response detector 204. The monitored electrocardiac response during the window is transmitted by evoked response detector 204 via conductor 208 to integration circuit 206 as shown in FIG. 2. It is only during this response window that evoked response detector 204 is activated to detect an evoked electrocardiac response from the heart.

During the response window, typically between 10 and 150 milliseconds, the electrocardiac response is integrated by integration circuit 206. The end of the evoked electrocardiac response is detected by timing and control circuit 207 in order to facilitate closing of the response window. Assuming no natural heartbeats occur during the response window, integration circuit 206 will output, at the end of the response window, a value equal substantially to the ventricular gradient of the patient's heart for the particular cardiac cycle. This ventricular gradient is transmitted via conductor 212 to timing and control circuit 207.

Included within timing and control 207 is a stored value of a critical ventricular gradient which represents a potentially pathological dispersion, i.e., the imminent onset of tachyarrhythmia. Such value may be determined by the physician and stored during the patient's visit with the physician. The critical value may be determined for each patient by the physician in accordance with techniques known in the medical field. Importantly, the pacing system never automatically varies the stored value from one cardiac cycle to the next.

When the ventricular gradient as output by integration circuit 206 increases beyond the stored value, timing and control circuit 207 responds by increasing the pacing rate in a controlled fashion. The increased pacing rate diminishes the dispersion and results in protection against the tachyarrhythmia. When the dispersion decreases to an acceptable level, the pacing rate returns to its normal value.

The above discussion assumed that all monitored electrocardiac activity resulted from the cardiac response to pulses generated by pacing system 100. Such is not the case as naturally occurring heartbeats may occur in between evoked responses and therefore interfere with the pacing cycle set forth by pacing system 100.

Spontaneous event detector 205 and associated circuitry provide a means of protecting naturally occurring heartbeats from interfering with the evoked pacing cycle. Specifically, spontaneous event detector 205 is enabled to monitor electrocardiac activity that occurs as a result of natural cardiac activity. Any such naturally occurring electrocardiac activity is detected by spontaneous event detector 205 and simultaneously by evoked response detector 204. Spontaneous event detector 205 then signals timing and control circuit 207, via conductor 211 and timing and control circuit 207, in response thereto, resets the entire system to the beginning of the cardiac cycle via conductors 210, 211 and 213 It should be noted that conductor 213 may actually be a three wire bus for conveying several signals to output and charge dump circuit 201 as discussed further in the previously incorporated U.S. Pat. No. 4,878,497.

After the entire system is reset to the beginning of a cardiac cycle, the naturally occurring cardiac activity will be monitored by spontaneous event detector 205 and integrated by integration circuit 206 just as if it were the evoked response to a pacing pulse from pacing system 100. As a result, the patient's heart 214 will simply experience two beats which are closer together in time than the normal pacing rate would have them. Thereafter, the patient's heart rate will return to the normal pacing rate.

Figure 3:
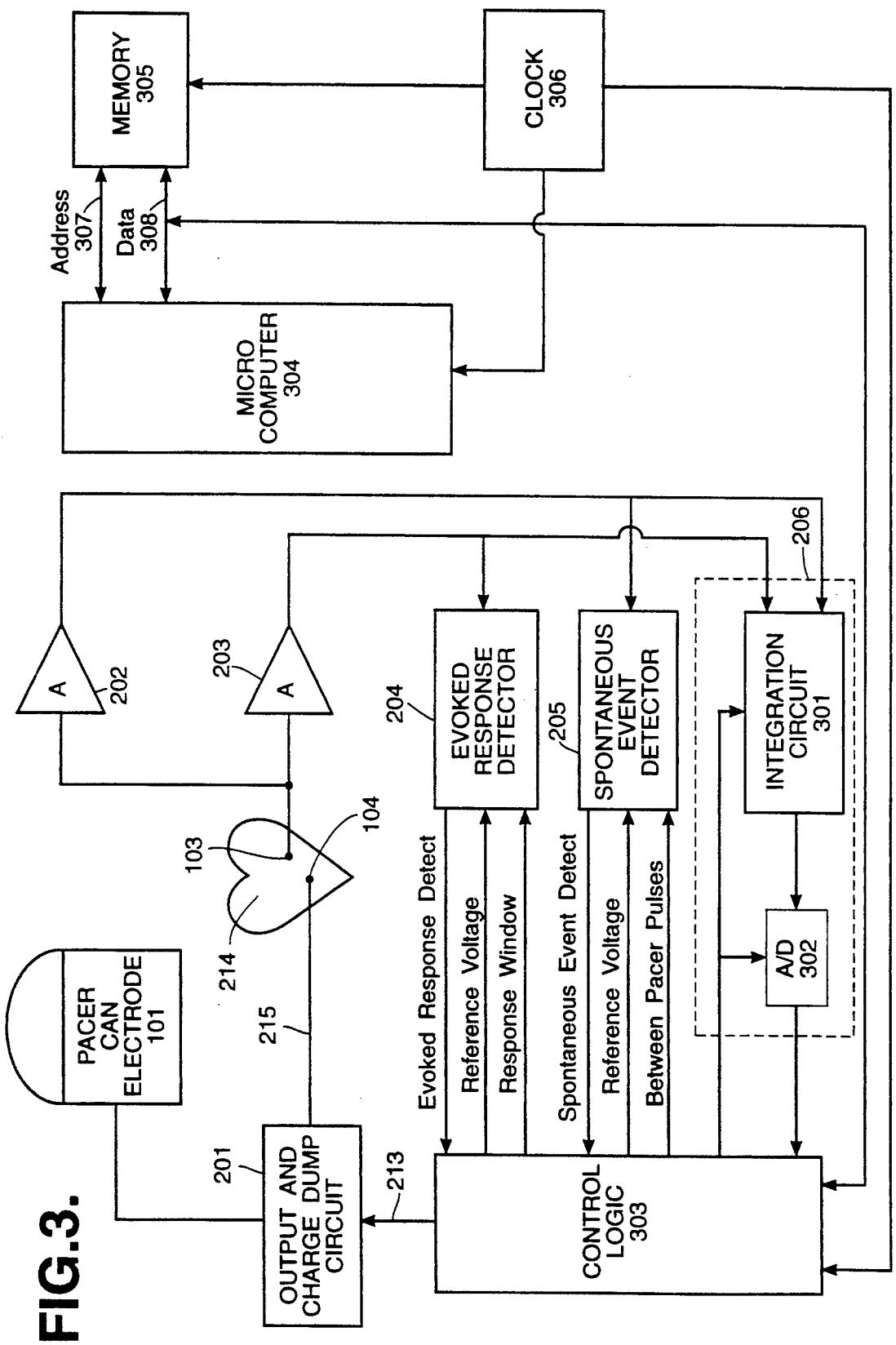
FIG. 3 is a more detailed diagram of the circuitry within the arrangement of FIG. 2.

A relatively detailed schematic diagram of the pacer circuitry is presented in FIG. 3. Referring to FIG. 3, it is seen that the same reference numerals are used for the same components of FIG. 2. Timing and control circuit 206 comprises a microcomputer 304 which communicates with memory 305 via address bus and data bus 307 and 308, respectively. Conventional control logic 303 is coupled to data bus 308, and a conventional crystal controlled clock 306 is used for providing appropriate clock pulses for the system. The functions of the control logic inputs and outputs are designated.

In operation, the beginning of an electrocardiac response is received by either of amplifiers 202 or 203, and is conveyed to evoked response detector 204 or spontaneous event detector 205. If a naturally occurring electrocardiac response is detected, then spontaneous event detector 205 asserts "spontaneous event detect" to control logic 303 as shown. Similarly, if the electrocardiac response detected is a result of the stimulation pulse from pacing system 100, then "evoked response detect"

is asserted by evoked response detector 204. The signals "between pacer pulses" and "evoked response window" serve to enable the proper response detector during the proper time in the cardiac cycle as previously described.

Upon detection of an electrocardiac response, control logic 303 enables integration circuit 206 and analog to digital (A/D) converter 302 as shown in FIG. 3. A digital version of the ventricular gradient will then be transmitted at the end of the response to microcomputer 304 for processing.

Microcomputer 304 communicates with memory 305 in order to compare the ventricular gradient associated with the cardiac cycle to the stored value via address and data buses 307 and 308, respectively. If the ventricular gradient equals or exceeds the stored value, microcomputer 304 signals control logic 303 and the pacing rate is adjusted accordingly. In this manner, the tachyarrythmia is prevented before it occurs by control logic 303 adjusting the parameters in the pacing system appropriately.

Figure 4:
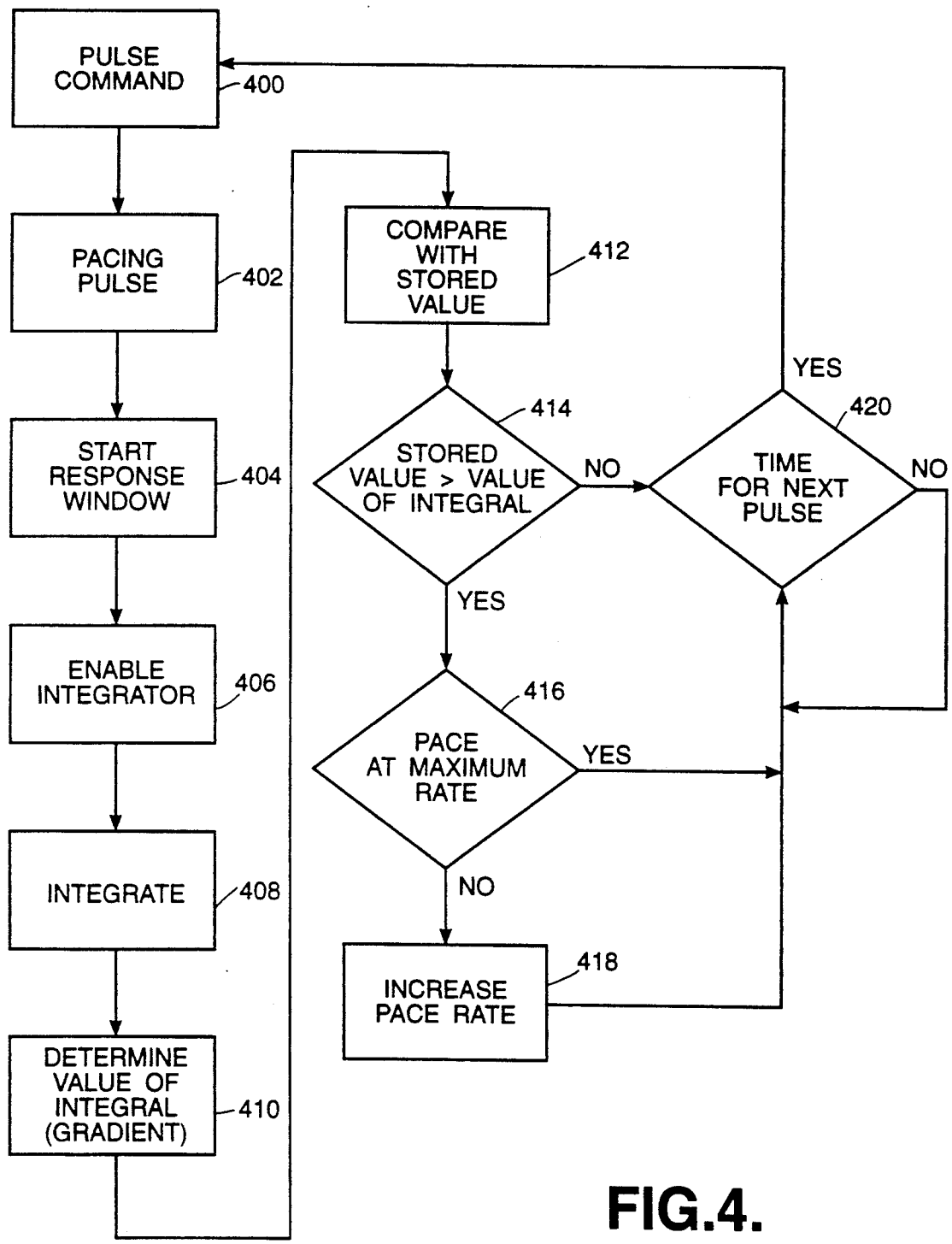
FIG. 4 is a flow chart of the operation of the pacing system described herein.

A flow chart illustrating the operation of the circuit of FIG. 3 is shown in FIG. 4. Such a flow chart may be implemented using many hardware arrangements which differ from that of FIG. 3.

The cycle begins with a pulse request (400) which causes a pacing pulse to be delivered to the heart through output and charge dump circuit 201 (402). After the pacing pulse is delivered, the response window previously discussed is opened (404) and the integration circuit 301 is enabled (406). The evoked electrocardiac activity is then detected and integrated (408) to determine the value of the ventricular gradient (410). The value of the ventricular gradient is compared with the stored value (412) to determine if the ventrical gradient for the cardiac cycle is greater than the stored value (414).

If the ventricular gradient is not greater than the stored value, indicating normal cardiac conditions, the pacing cycle remains the same and decision branch 420 simply waits until it is time for the next pacing pulse. If the ventricular gradient is greater than the stored value, decision branch 416 checks to determine if the pacing rate is already at its predetermined maximum rate, where the predetermined maximum rate was set previously by the physician. If the pacing rate is not at its maximum, it may be increased by operational block 418 which adjusts a timer (not shown), so that decision block 420 will transfer control to operational block 400 in less time than during the previous cardiac cycle, thereby increasing the pacing rate. If the pacing rate is already at its maximum, then the pacing rate will remain the same and control will be transferred to operational block 420 by decision branch point 416.

It is also important that after the ventricular gradient is reduced to an acceptable level, the pacing rate return to its normal value. Although this is not shown in FIG. 4, this can be implemented at decision branches 414 and 420. Specifically, if the ventricular gradient is below the predetermined value, yet the pacing rate is abnormally high, then the decision branch point 420 would readjust the time to slow the pacing rate.

The important result is that the pacer diagnoses a deteriorating heart and corrects it before the tachyarrhythmia even occurs, rather than attempting to correct a tachyarrythmia condition after occurrence.

It is understood that the above-described implementation is the preferred embodiment of the invention, and that many other variations will be apparent to those of ordinary skill in the art. For example, microcomputer 304 may be replaced with discrete logic or integration circuit 206 may be replaced with a digital integrator which approximates the exact integral of the electrocardiac response. Additionally, amplifiers 202 or 203 may be replaced with many other types of amplifiers which are well known in the art. It is also possible that the patient's normal heartbeat; i.e. without the use of a pacing system be monitored, and that the pacing system be invoked only to prevent the tachyarrythmia.

Many other variations of the invention will be apparent to those of ordinary skill in the art, and such variations do not violate the spirit and scope of the invention.

I claim:

1. A cardiac pacing system for preventing tachyrhythmia of a heat comprising:
   means for integrating at least a portion of an electrocardiac response from the heat to obtain a gradient;
   means responsive to said integrating means for determining that an arrhythmia is impending if said gradient is above a predetermined value; and
   means responsive to said determining means for generating pacing pulses at a predetermined elevated rate when said determining means indicates that an arrhythmia is impending such that said arrhythmia is prevented.

2. The cardiac pacing system of claim 1 further comprising means for generating pacing pulses at a predetermined unelevated rate if said determining means does not indicate that an arrhythmia is impending.

3. The cardiac pacing system of claim 2, wherein said means for integrating comprises means for integrating an entire QT waveform associated with said electrocardiac response to obtain a ventricular gradient.

4. A cardiac pacing system according to claim 3 further comprising a spontaneous event detector for detecting naturally occurring electrocardiac activity during an electrocardiac response to a generated pacing pulse; and
   means for resetting said pacing system such that said gradient obtained is that resulting from said naturally occurring electrocardiac activity.

5. A cardiac pacing system according to claim 2, wherein said means for integrating, means for determining and means for generating, are all microcomputer controlled.

6. A cardiac pacing system according to claim 3, wherein said means for integrating, means for determining and means for generating, are all microcomputer controlled.

7. A cardiac pacing system according to claim 1, wherein said means for integrating, means for determining and means for generating are microcomputer controlled.

8. A cardiac pacing system according to claim 1 further comprising a power source and an output and charge dump circuit connected between said power source and said heart for conveying an electric charge tot he heart and for providing substantially instantaneous discharge therefrom.

9. A cardiac pacing system according to claim 1 further comprising a timing and control means coupled to said means for integrating, to said means for determining and to said means for generating, for enabling each of said means at selected times during a cardiac cycle.

10. A cardiac pacing system for pacing a heart at a selected pacing rate comprising:

means for monitoring electrocardiac response and for obtaining a gradient therefrom;

means for determining from said gradient if a tachyarrhythmia is about to occur in the heart; and means for varying the pacing rate such that said tachyarrhythmia is prevented.

11. The cardiac pacing system of claim 10, wherein said means for varying the pacing rate includes means for increasing the pacing rate.

12. The cardiac pacing system of claim 11, wherein said means for determining comprises an integrator arranged to integrate an electrocardiac response generated by the heart;

a digital memory; and digital microcomputer means for comparing the integrated response to a predetermined value stored in said digital memory.

13. A cardiac pacing system according to claim 12, wherein said means for monitoring comprises;

means for monitoring evoked electrocardiac activity; and means for monitoring naturally occurring electrocardiac activity.

14. A cardiac pacing system according to claim 11 wherein said gradient is a ventricular gradient.

15. A cardiac pacing system according to claim 11, wherein said means for determining includes an A/D converter for converting said gradient to digital form.

16. A cardiac pacing system according to claim 11, wherein said means for monitoring comprises:

means for monitoring evoked electrocardiac activity; and means for monitoring naturally occurring electrocardiac activity.

17. A cardiac pacing system according to claim 12, wherein said means for determining includes an A/D converter for converting said gradient to digital form.

18. A cardiac pacing system according to claim 10, wherein said means for monitoring comprises:

means for monitoring evoked electrocardiac activity; and means for monitoring naturally occurring electrocardiac activity.

19. A cardiac pacing system according to claim 10, wherein said means for determining includes an A/D converter for converting said gradient to digital form.

20. A cardiac pacing system according to claim 10 wherein said gradient is a ventricular gradient.

* * * * *

UNITED STATES PATENT AND TRADEMARK OFFICE
CERTIFICATE OF CORRECTION

PATENT NO. : 5,271,393

DATED : December 21, 1993

INVENTOR(S) : Callaghan

It is certified that error appears in the above-identified patent and that said Letters Patent is hereby corrected as shown below:

Col. 6, line 17, the word "heat" should read --heart--

Col. 6, line 19, the word "heat" should read --heart--

Signed and Sealed this

Twenty-third Day of August, 1994

Attest:

BRUCE LEHMAN

Attesting Officer

Commissioner of Patents and Trademarks